United States Patent [19]
Li

[11] Patent Number: 4,825,010
[45] Date of Patent: Apr. 25, 1989

[54] ISOMERIZATION OF BY-PRODUCTS OF BI-PHENOL SYNTHESIS

[75] Inventor: Simon M. Li, Houston, Tex.

[73] Assignee: Shell Oil Company, Houston, Tex.

[21] Appl. No.: 109,894

[22] Filed: Oct. 19, 1987

[51] Int. Cl.⁴ .................. C07C 37/68; C07C 39/16
[52] U.S. Cl. ............................. 568/724; 568/722; 568/723; 568/724; 568/727; 568/728
[58] Field of Search ............. 568/722, 723, 724, 727, 568/728

[56] References Cited

U.S. PATENT DOCUMENTS

| | | |
|---|---|---|
| 3,221,061 | 11/1965 | Grover et al. .................. 568/727 |
| 4,239,919 | 12/1980 | Hairston .......................... 568/727 |
| 4,375,567 | 3/1983 | Faler ............................... 568/727 |
| 4,400,555 | 8/1983 | Mendiratta ..................... 568/728 |
| 4,584,416 | 4/1986 | Pressman ........................ 568/727 |
| 4,590,303 | 5/1986 | Mendiratta ..................... 568/728 |

FOREIGN PATENT DOCUMENTS 2201833 9/1987 Japan ................................ 568/722

Primary Examiner—Werren B. Lone

[57] ABSTRACT

By-products of bis-phenol synthesis are isomerized in the presence of a mercapto modified cation exchange resin catalyst.

24 Claims, 1 Drawing Sheet

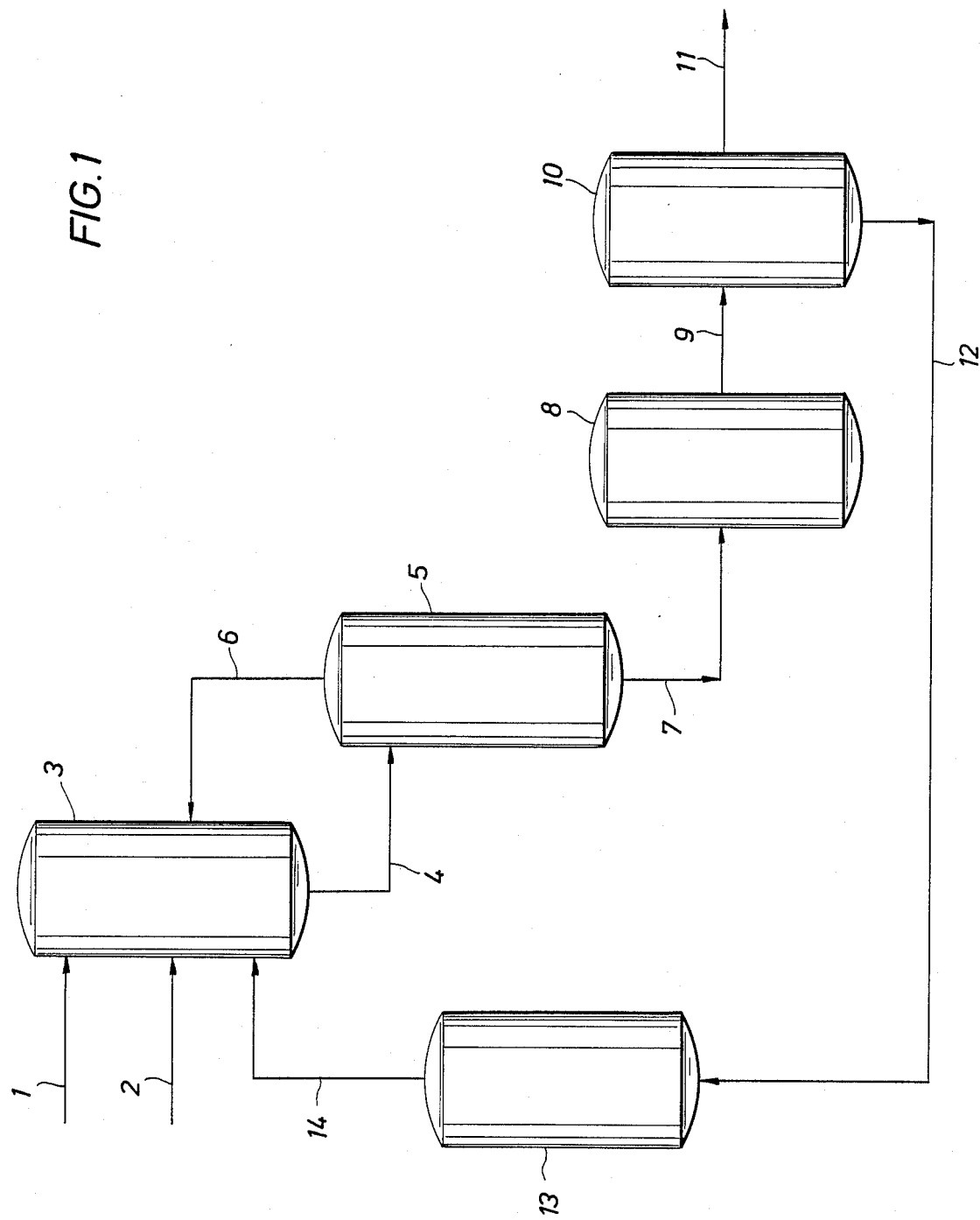

ISOMERIZATION OF BY-PRODUCTS OF BI-PHENOL SYNTHESIS

FIELD OF THE INVENTION

The present invention relates to the isomerization of by-products from the preparation of a bis-phenol.

BACKGROUND OF THE INVENTION

Many processes are known to prepare bis-phenol-A. In some of these processes phenol is reacted with acetone to form bis-phenol-A. It is customary to then isolate the bis-phenol-A by crystallization, distillation or adduct crystallization. The concentrated residue contains many isomerizable components, such as o,p'-bis-phenol-A and other variations from bis-phenol-A. These components of the residue are usually isomerized in an acidic medium to the desired bis-phenol-A. The acidic medium includes inorganic acids such as hydrochloric acid and acidic cation exchange resins.

U.S. Pat. No. 3,221,061 discloses the preparation of bis-phenol-A and a subsequent "rearrangement" reaction conducted in the presence of a phenol saturated (mercapto alcohol modified) cation exchange resin.

U.S. Pat. No. 4,400,555 discloses a multi-step synthesis in which acetone is injected in portions and an isomerization follows but the patent fails to illustrate the kind of catalyst in the isomerization zone.

U.S. Pat. No. 4,590,303 discloses a similar process in which the catalyst in the "rearrangement" reaction is a mercapto modified macroporous ion exchange resin and the acetone is injected into the "rearrangement" reactor. While the total conversion of acetone was increased, the percentage of undesired by-products also increased. However, from the data in the experiments in this patent, it can be seen that diverting a part of the acetone to the "rearrangement" reactor was adverse to isomerization since the selectivity to the desired bis-phenol-A became progressively worse. Thus, the desired isomerization was not demonstrated.

U.S. Pat. No. 4,375,567 discloses that both micoreticular and macroreticular ion exchange resins in an unmodified form are used for isomerization. In this case, the microreticular resins were less effective for isomerization than the macroreticular resins.

There still exits a need to reduce or utilize the amount of undesirable by-products from the preparation of bis-phenols, e.g. bis-phenol-A from phenol and acetone. Obviously, the art has failed to find a method to react the two starting materials without the production of by-product isomers. Thus, there is still a need to more effectively convert these undesired isomers into the desired bis-phenol. The present invention addresses this problem and provides a new method to isomerize the undesired by-products to the desired bis-phenol.

SUMMARY OF THE INVENTION

The present invention is directed to a process for isomerizing the by-products from the preparation of a bis-phenol in the desired 4.4'-dihydroxy form from a phenol and a ketone, which comprises treating the by-products from the preparation of bis-phenol from a ketone and phenol with a catalytic amount of an acidic sulfonated cationic exchange resin having a plurality of sulfonic acid sites ionically bonded to an alkylmercaptoamine to isomerize the by-products and recovering an isomerization product having a higher concentration of the desired bis-phenol having the 4,4'-dihydroxy form.

The present invention is useful in recovering more of a desired bis-phenol, e.g. bis-phenol-A, by isomerization of an undesired bis-phenol such as 2,4'-dihydroxy-2,2-diphenyl propane (commonly referred to as o,p'-BPA) and related by-products to the desired bis-phenol-A with less formation of certain other undesirable impurities such as 1,3,3-trimethyl-p-hydro-xyphenyl-6-hydroxyindane, 4-methyl-2,4-bis-(4'-hydroxyphenyl)-pentene-2 and the like.

The present invention is useful for the isomerization of certain undesirable by-products from the preparation of a bis-phenol from a ketone and a phenol. The bis-phenols include those prepared by the reaction of a ketone, such as acetone, ethyl methyl ketone, isobutyl methyl ketone, acetophenone, cyclohexanone, 1,3-dichloro acetone and the like, with a phenol, such as phenol, o-cresol m-cresol, o-chlorophenol, m-chlorophenol, o-t-butylphenol, 2,5-xylenol, 2,5-di-t-butylphenol o-phenylphenol and the like. The above is not meant to limit the invention but to illustrate representative examples of ketones and phenols which are known in the art to make desirable bis-phenol and for which those of skill in the art can substitute other conventional bis-phenol reactants.

The catalysts for the isomerization are alkylmercaptoamine-modified acidic sulfonated cation exchange resins in which the alkylmercaptoamine contains from about 1–30 carbon atoms. Such resins which can be used as catalysts are conventionally known in the art and include those acidic cation exchange resins that are modified by conventional procedures known in the art with an alkylmercaptoamine modifying agent of the invention either before use in the isomerization process or in some cases modified by the addition of the mercapto modifying agent to the isomerization process for use in conjunction with the previously unmodified acidic cation exchange resin. The alkylmercaptoamines include propylaminopropylmercaptan, cysteamine or preferably an alkylmercaptoamine having at least two alkylmercaptan branches, such as a material of Formula I

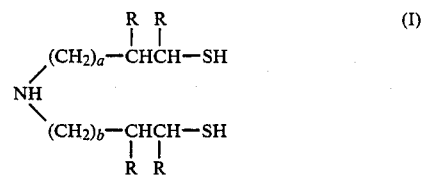

each of a and b is an integer from 0 to about 5 and each R is selected independently from H, OH, SH, and alkyl groups containing from about 1 to 4 carbon atoms. As can be seen from the formula, the latter catalyst contains a high acidity density per given mercaptan concentration or a higher mercaptan concentration per given residual acidity density, as compared to cationic exchange resin catalysts modified with monofunctional mercaptan alcohol promoters. The catalyst exhibits high activity and selectivity at moderate reaction temperatures, low production of colored impurities and good stability.

The preparation of the aminomercaptan modifier of Formula I can be carried out by halogenating a diolefinic amino compound of the general formula

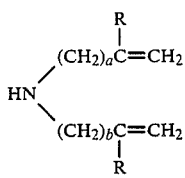

and which a, b and R are as described above.

Such compounds include, for example, the diallylamine in which a and b are 1. Alternately, the modifier can be prepared by starting with a secondary amine containing multiple alkyl halides of the general formula

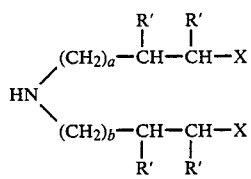

in which R' is selected independently from H, Cl, Br, I and alkyl groups containing about 1 to 4 carbon atoms, and each X is independently chosen from Cl, Br and I. Such compounds include, for example, the bis-2-haloethylamine. The above halogen-containing amine salt, for example the bis-2-halogenethyl amine hydrochloride salt, is reacted with sodium thioacetate in an alcoholic medium such as ethanol. The resulting bis-(2-thioacetylethyl)acetamide can be acid neutralized by hydrolysis and reacted with sulfonyl groups of the cationic exchange resin by reflux together in aqueous alcoholic solution with an optional reducing agent such as triphenyl phosphine. The modified resin is then washed with an aqueous alcohol in solution and dried in a vacuum at about 50°–100° C. The resulting modified resins are also disclosed in Applicant's copending U.S. Ser. No. 925,779, filed Oct. 30, 1986.

The currently preferred modified cationic exchange resin catalysts of the invention can be described by the Formulas II and III

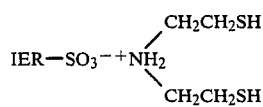

and

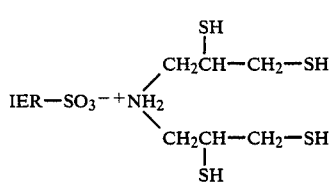

in which IER represents the ionic exchange resin backbone.

The modified catalyst will generally have from about 2 mole percent to about 25 mole percent of mercapto-modified acidic groups, preferably from about 3 mole percent to about 50 mole percent.

The resins effectiveness in the mercapto modified resin isomerization process of the invention is to some extent influenced by their exchange capacities such that the greater the exchange capacity then the more desirable the resin is for isomerization. Preferably, the cation exchange capacity is at least about 0.5 and, preferably greater than 4.0 meq/g dry weight. Also, those cation exchange resins having bound cationic exchange groups of the stronger exchange potential acids are preferred for use in the mercapto modified resin isomerization process of the present invention. Acidic cation exchange resins suitable for modification with a mercapto modifying agent for use in isomerization include sulfonated styrene-divinylbenzene copolymers, sulfonated cross-linked styrene polymers, phenol-formaldehyde-sulfonic acid resins, benzene-formaldehyde-sulfonic acid resins and the like. These include resins under such tradenames as Amberlites (Rohm and Haas Co.), DOWEX ® (Dow Chemical Co.), Permutit QH (Permutit CO.), Chempro (Chemical Process Co.), Lewatit (Bayer A.G.) and the like. Strong acid sulfonated styrene-divinylbenzene copolymer resins are preferred. Commercially available aromatic sulfonic acid resins are generally obtained as sodium salts and are converted to the acid form prior to use. Both modified macroreticular resins and microreticular resins are useful in the isomerization process of the present invention. The choice of resin will of course depend on the material to be isomerized, the reaction conditions and the effect of an individual resin under the conditions selected, which determination and selection is within the skill of the art. Macroreticular resins are preferred.

The precise catalytic amount of mercapto-modified acidic cation exchange resin to be used will usually vary to some degree depending on the specific resin, feed and conditions used for isomerization process. By way of illustration, the catalyst can be present from about 0.05 lbs per lb of feed per hour to about 10.0 lbs per lb of feed per hour and preferably from about 0.2 lbs to about 2 lbs per lb of feed per hour.

The isomerization is usually conducted in the presence of minor amounts of water in the reaction solution of from about 1.5% to essentially anhydrous conditions based on the isomerization reaction solution. Somewhat higher amounts of water can be present but this could result in less desirable rate of reaction. Somewhat higher amounts of water can also decrease net formation of the non-reversible impurities in the desired product. Preferably, the water content of the reaction solution is from about 0.1% to about 0.7% based on the isomerization reaction solution.

The isomerization reaction is usually conducted at moderately elevated temperatures. Suitable temperature are from about 50° C. to about 110° C. at ambient pressure. Preferably, the reaction temperature is from about 60° C. to about 85° C. at ambient pressure.

Thus, the isomerization reaction is conducted by contacting a feed stream containing liquid by-products from the preparation of a bis-phenol, such as 2,4'-dihydroxy-2,2-diphenyl propane and related by-products and optionally (phenol) washings from the crystallization of bis-phenol-A, with an acidic sulfonated cationic exchange resin having a plurality of sulfonic acid sites ionically bonded to a group of the Formula I

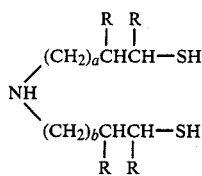

(I)

under moderately elevated temperatures and in the presence of some water. The feed stream passes through the resin catalyst for a period of time sufficient to effect isomerization depending on the feed rate, size of the resin bed, the particular mercapto modified resin used and the like as can readily be determined by those of skill in the art. The resulting isomerization product enriched in the desired bis-phenol having a 4,4'-dihydroxy form, such as bis-phenol-A, is then recovered. Usually the recovered product is recycled back to a zone in which the bis-phenol is prepared by condensation of a ketone (acetone) and phenol.

The reaction time in the isomerization or in the condensation depends on the reaction temperature and other reaction conditions, including whether the process is continuous or batch processing.

Another embodiment of the present invention is directed to a process for the preparation of a bis-phenol having a desired 4,4'-dihydroxy form which comprises (a) condensing a ketone, such as acetone, and a phenol in the presence of an acid, such as an acidic cation exchange resin, (b) crystallizing an adduct of the phenol and the desired bis-phenol to obtain the desired bis-phenol, and (c) isomerizing the by-products of the condensation step (a) optionally with any wash liquids from the crystallization step (b) in the presence of a mercapto modified cation exchange resin catalyst to obtain a product enriched in the desired bis-phenol for recycle to the condensation step (a).

The condensation of acetone and phenol can be conducted using cation exchange resin conventionally known in the art for the condensation of acetone and phenol. In general, these are often mercapto modified resins of the type conventionally known in the art which include any compound which will react with the acidic groups of the cation exchange resin to introduce a mercapto substituent into the resin. Suitable mercapto modifying agents include simple alkyl mercaptans, alkyl mercapto amines, mercapto alcohols, and precursors and the like, for example, methyl mercaptan, propylaminopropyl mercaptan, mercaptan, bis-2-(mercaptoethyl)-amine, mercapto ethanol, thiazolidine and the like, although unmodified resins are also useful.

The condensation reaction is conducted at moderately elevated temperature of from about 50° C. to about 130° C. at ambient pressures.

In the preparation of the bis-phenols, an excess of the phenol is usually desirable, generally from about 5 to about 20 moles of phenol per mole of ketone, is desirable for high conversion of the ketone. Solvents or diluents are not necessary in either the preparation of the bis-phenol or in the isomerization of the undesired by-product except at low temperature.

The bis-phenol product, e.g., bis-phenol-A, is passed to a concentrator where the acetone and phenol and excess water are removed as an overhead fraction. The crude bis-phenol-A product is then passed to a crystallization zone where it is chilled to about 30° C. to about 95° C. to form an adduct of phenol and bis-phenol-A which separates out as crystals. After washing with phenol, filtering and the like, the bis-phenol-A is recovered from the adduct. The mother liquid by-product stream from the crystallization zone is passed to the isomerization zone, optionally combined with the phenol washings from the crystallization step, and isomerized in the presence of a mercapto modified cation exchange resin catalyst as described above. The product of this isomerization enriched in bis-phenol-A is recovered or preferably recycled to the condensation zone.

BRIEF DESCRIPTION OF THE DRAWING

FIG. 1 is a schematic drawing of a process to prepare bis-phenol-A in which acetone and phenol are reacted to form bis-phenol-A and the by-product isomers are subsequently treated in the presence of mercapto modified cation exchange resin and in which both the preparation of bis-phenol and the isomerization take place in the presence of mercaptan modified resins.

DETAILED DESCRIPTION OF THE DRAWING

With reference to FIG. 1, acetone and phenol reactants are injected into a condensation reactor 3 via lines 1 and 2, along with any recycle isomerization product added via line 14. Any conventional condensation catalyst effective for the formation of bis-phenol-A can be used. However, it is advantageous that the reactor contains an unmodified or modified cation exchange resin, such as a macroreticular sulfonated polystyrene divinylbenzene acidic cation exchange resin at about 50° to 90° C. The reaction product is passed via line 4 into a concentrator 5 in which unreacted acetone and phenol and excess water are recovered for recycle via line 6 to zone 3 and crude bis-phenol-A product is recovered and passed via line 7 to crystallizer 8 to form a solid bis-phenol-A/phenol adduct. The slurry is passed via line 9 into separator 10 wherein the adduct is separated from the by-product mother liquid and is passed via line 11 into a melter (not shown). The by-product mother liquid is removed from the separator 10 and passed via line 12 into an isomerization zone 13. The isomerization zone is maintained at about 60°-90° C. and contains an acidic cationic exchange resin which is used in a mercapto modified form. This is conveniently microreticular or macroreticular acidic cation exchange resin such as sulfonated styrene-divinylbenzene modified with about 10% of bis-2-(mercaptoethyl)-amine. The isomerization product which is increased in concentration of the desired bis-phenol-A is recycled to the condensation reactor via line 14.

While the invention has been illustrated with particular apparatus, those of skill in the art will appreciate that equivalent or analogous apparatus or parts thereof can be employed and that the use of equipment operated in series of in parallel can be used. Batch of continuous form can be used. The solid catalysts can be used as a slurry with the reactants in batch processing or in a fixed bed in a continuous process.

ILLUSTRATIVE EMBODIMENT

The invention is illustrated by the following embodiments which should not be regarded as limiting the invention in any way.

EMBODIMENT 1

Experiments were performed in batch at 80° C. using a 1:3 catalyst to reactant weight ratio for the following systems: (1) unmodified macroporous DOWEX MSC- 1; (2) 10% bis-2-(mercaptoethyl)amine (BMEA) modified macroporous DOWEX MSC-1. Each catalyst was pre-dried in vacuum oven at 60°–70° C. for 1–2 days and the reactant source was by-product from bis-phenol-A obtained by the condensation of acetone and phenol containing 2,4′-dihydroxy-2,2-diphenyl propane. CDB (1,3,3-trimethyl-p-hydroxyphenyl-6-hydroxyindane) and LDP-1 (4-methyl-2,4-bis-(4′-hydroxyphenyl)pentene-2) are undesirable by-products of isomerization with unmodified catalysts and are also present in the isomerization feed.

Results are given in Table 1 and illustrate that the desired isomerization took place with the modified catalyst but that no additional CDB or LDP-1 or heavies and unknowns were obtained.

TABLE 1

Summary of Batch Isomerization of By-products from Bis-phenol-A Synthesis

| System[a] | % w Water[b] | Δ CDB/LDP-1[c] (ppm) | Δ Heavies[c] or Unknown (ppm) |
|---|---|---|---|
| 1 | 0.22 | 5000 | 250 |
|   | 0.35 | 1500 | 50 |
| 2 | 0.36 | — | — |

[a]System: 1. Unmodified macroporous DOWEX MSC-1.
2. 10%-BMEA modified macroporous DOWEX MSC-1.
[b]Water in solution phase.
[c]Net increase at 80° C. after 50% of isomerizable o,p′-BPA has been converted to p,p′-BPA.

EMBODIMENT 2

Following procedures similar to those described in Embodiment 1 above, by-products from the preparation of bis-phenol-A were isomerized with a 15% bis-2-(mercaptoethyl)-amine modified microreticular DOWEX 50WX2 resin in the presence 0.35% w water in the reactant solution. No Δ CDB/LDP-1 was obtained after 50% of the isomerizable o,p′-BPA has been converted to p,p′-BPA, although some heavies and a new impurity were obtained.

What is claimed is:

1. A process for isomerizing the by-products from the preparation of a desired bis-phenol having a 4,4′-dihydroxy form which comprises treating the by-products from the preparation of the desired bis-phenol from the condensation of a ketone with a phenol, at about 50° C. to about 110° C. and at about ambient pressure with a catalytic amount of a sulfonated cationic exchange resin having a plurality of sulfonic acid site ionically bonded to an alkylmercaptoamine and a minor amount of water up to about 1.5 percent weight based on the isomerization reaction solution to isomerize the undesired by-products and recovering a product having a higher concentration of the desired bis-phenol.

2. A process according to claim 1 wherein the resin is modified with an alkylmercaptanamine of the Formula I

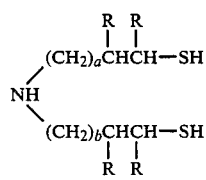

3. A process according to claim 2 wherein the resin has the Formula II or III

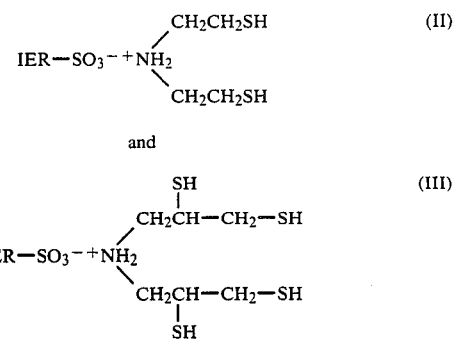

in which IER represents the ionic exchange resin backbone.

4. A process according to claim 1 wherein the resin is selected from sulfonated styrene-divinylbenzene copolymers, sulfonated cross-linked styrene polymers, phenol-formaldehyde-sulfonic acid resins, or benzene-formaldehyde-sulfonic acid resins.

5. A process according to claim 4 wherein the resin is a sulfonated styrene-divinylbenzene copolymer.

6. A process according to claim 5 wherein the resin is a macroreticular resin.

7. A process according to claim 5 wherein the resin is a microreticular resin.

8. A process according to claim 1 wherein the by-products are from the preparation of bis-phenol-A and included undesired 2,4′-dihydroxy-2,2-diphenyl propane.

9. A process according to claim 8 wherein the resin is a sulfonated styrene-divinylbenzene copolymer.

10. A process according to claim 9 wherein the resin is modified with an alkylmercaptanamine of Formula I

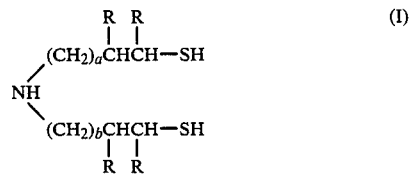

11. A process according to claim 10 wherein the resin has the Formula II or III

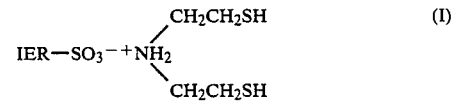

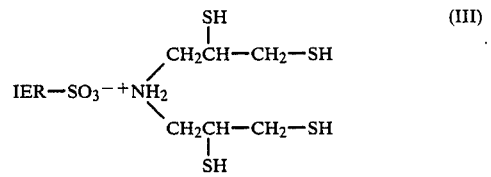

in which IER represents the ionic exchange resin backbone.

12. A process for the preparation of a bis-phenol which comprises (a) condensing a ketone and a phenol in the presence of an acidic cation exchange resin, (b)

crystallizing an adduct of the phenol and the desired bis-phenol to obtain the desired bis-phenol, and (c) isomerizing the by-products of step (a) with any phenol wash liquids from the crystallization step (b) at about 50° C. to about 110° C. and at about ambient pressure in the presence of a sulfonated cationic exchange resin having a plurality of sulfonic acid sites ionically bonded to an alkylmercaptoamine and a minor amount of water of up to about 1.5% weight based on the isomerization reaction solution to obtain a product enriched in the desired bis-phenol for recycle to condensation step (a).

13. A process according to claim 12 wherein the resin is in the isomerization modified with an alkyl of the Formula I

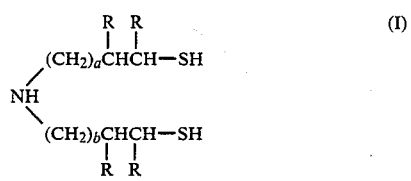

14. A process according to claim 13 wherein the resin has the Formula II or III

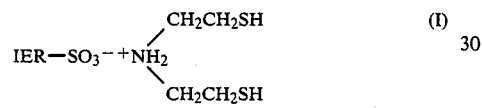

and

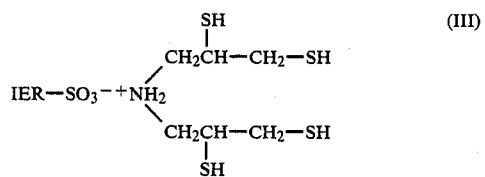

in which IER represents the ionic exchange resin backbone.

15. A process according to claim 12 wherein the resin is selected from sulfonated styrene-divinylbenzene copolymers, sulfonated cross-linked styrene polymers, phenol-formaldehyde-sulfonic acid resins, or benzene-formaldehyde-sulfonic acid resins.

16. A process according to claim 15 wherein the resin in the condensation or isomerization is a sulfonated styrene-divinylbenzene copolymer.

17. A process according to claim 16 wherein the resin in the isomerization is a macroreticular resin.

18. A process according to claim 16 wherein the resin in the isomerization is a microreticular resin.

19. A process according to claim 12 wherein the resin in the condensation step (a) is an unmodified resin.

20. A process according to claim 12 wherein the resin in the condensation step (a) is a mercapto modified resin.

21. A process according to claim 12 for the preparation of bis-phenol-A and wherein the by-products included undesired 2,4'-dihydroxy-2,2-diphenyl propane.

22. A process according to claim 21 wherein the resin in the isomerization is a sulfonated styrene-divinylbenzene copolymer.

23. A process according to claim 22 wherein the resin is modified with an alkylmercaptanamine of the Formula I

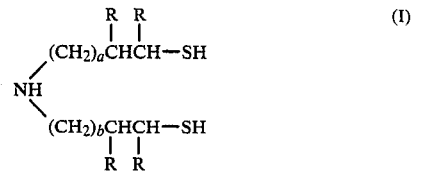

24. A process according to claim 23 wherein the resin has the Formula II or III

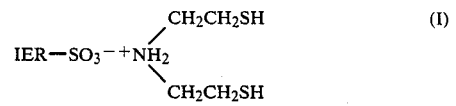

and

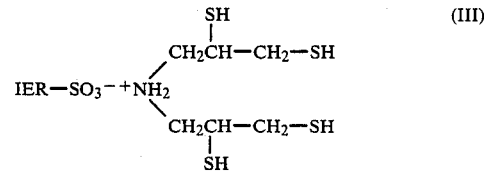

in which IER represents the ionic exchange resin backbone.

* * * * *